United States Patent [19]

Wachtler et al.

[11] Patent Number: 5,354,777

[45] Date of Patent: Oct. 11, 1994

[54] CYANOALKENE DERIVATIVES, PROCESS FOR THEIR PREPARATION, AND THEIR USE AS MICROBICIDE FOR THE PROTECTION OF MATERIALS

[75] Inventors: Peter Wachtler, Köln; Wilfried Paulus; Georg-Wilhelm Ludwig, both of Krefeld, all of Fed. Rep. of Germany

[73] Assignee: Bayer Aktiengesellschaft, Leverkusen, Fed. Rep. of Germany

[21] Appl. No.: 21,407

[22] Filed: Feb. 23, 1993

[30] Foreign Application Priority Data

Mar. 2, 1992 [DE] Fed. Rep. of Germany ....... 4206528

[51] Int. Cl.$^5$ ..................... A01N 47/48; C07C 331/12
[52] U.S. Cl. ........................ 514/514; 558/10; 558/14; 558/17; 558/390; 558/395; 558/396; 558/397; 558/401; 558/430; 558/436; 558/437; 558/438; 558/452; 558/457
[58] Field of Search .................... 558/10, 14; 514/514

[56] References Cited

U.S. PATENT DOCUMENTS 3,991,050  11/1976  Cresswell et al. ............... 260/240 R
4,258,045   3/1981  Poe et al. ............................ 424/251

FOREIGN PATENT DOCUMENTS 0237516  9/1987  European Pat. Off. .
0266549  5/1988  European Pat. Off. .
0403884  4/1992  European Pat. Off. .
2094335  2/1972  France .

OTHER PUBLICATIONS

Drechsler, D. D., C.A., vol. 63, (1965), 4232h to 4233e.
Synth. Commun. 15 (1985) 12, p. 1067; Drecoes et al. (Incomplete Article).
Chemical Abstracts, vol. 73, (1970), p. 304, 14120h; Zedenin, et al.
Chemical Abstracts vol 76, (1972); p. 351, 14144f; Miyoji et al.
Bulletin de la Societe Chimique de france, pp. 2065–2071, (1974), Danion, et al.
vol. 95, (1981,) p. 713, 95:4250j; Popandova-Yambolieva et al.
Journal of Medicinal Chemistry, vol. 32, No. 8, Aug. 1989, pp. 1895–1905; Selassie, et al.
The Journal of Organic Chemistry, vol. 41, No. 20, Oct. 1, 1976, pp. 3241–3245; Cromwell et al.

*Primary Examiner*—Joseph Paul Brust
*Attorney, Agent, or Firm*—Sprung Horn Kramer & Woods

[57] ABSTRACT

New cyanoalkene derivatives of the formula (I)

$$R-CH=C(CN)-CH_2-R^1 \quad (I)$$

are described, in which R and R$^1$ have the meaning given in the description, and a process for their preparation.

The new cyanoalkene derivatives are used for combating microorganisms for the protection of industrial materials.

7 Claims, No Drawings

CYANOALKENE DERIVATIVES, PROCESS FOR THEIR PREPARATION, AND THEIR USE AS MICROBICIDE FOR THE PROTECTION OF MATERIALS

The invention relates to new cyanoalkene derivatives, to a process for their preparation, and to their use as microbicide for the protection of materials.

It has already been disclosed that the dibromopropanol derivatives described in EP-A-403,884 have microbicidal properties. However, due to their chemical reactivity in an alkaline medium such as, for example, dispersion paints, these compounds are not particularly stable. This disadvantage is avoided by the compounds according to the invention.

The application therefore relates to cyanoalkene derivatives of the formula

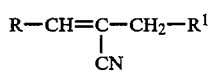  (I)

in which
represents optionally substituted $C_1$–$C_{12}$-alkyl, alkoxyalkyl, alkylmercaptoalkyl, cycloalkyl, $C_2$–$C_8$-alkenyl, cycloalkenyl, aryl, aralkyl, arylalkenyl or hetaryl and
$R^1$ represents NH—$R^2$,

S—$R^5$, SO—$R^5$, $SO_2R^5$,

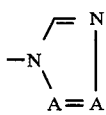

CN, NCS or SCN, where
$R^2$ represents alkyl, aryl or aralkyl and
$R^3$ and $R^4$ represent alkyl, aryl or aralkyl or
$R^3$ and $R^4$ form a six-membered aliphatic ring which is interrupted by O or N and which can be substituted by one or two methyl groups,
$R^5$ denotes alkyl, aryl or aralkyl and
A represents CH or N,
with the exception of compounds in which
R represents phenyl and
$R^2$ represents tert.-butyl, or
$R^3 = R^4$ represents $C_2H_5$ or $^iPro$ or

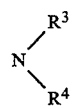

=piperidine or is morpholine.

Alkyl, individually or in composite radicals, hereinafter represents $C_1$–$C_{12}$-alkyl, preferably $C_1$–$C_6$-alkyl such as methyl, ethyl, n-propyl, i-propyl, n-butyl, tert.-butyl, n-hexyl, i-octyl and the n-dodecyl, each of which is optionally substituted by halogen atoms such as fluorine, chlorine or bromine or hydroxyl, for example trifluoromethyl or trichloromethyl, 2-methoxymethyl, 2-ethoxyethyl, 2-chloroethyl, 2-trifluoromethylmercaptoethyl, 2,3-dibromopropyl, hydroxyethyl and methylthioethyl.

Cycloalkyl hereinafter represents cycloalkyl having 5 to 7 carbon atoms, preferably cyclohexyl and cyclohexyl radicals which are substituted by halogen, in particular chlorine atoms and/or $C_1$–$C_4$-alkyl groups, such as 4-methylcyclohexyl, 2,6-dimethylcyclohexyl and 4-tert.butylcyclohexyl.

Alkenyl hereinafter represents alkenyl with 2 to 6 carbon atoms, preferably allyl, penten-1-yl or penten-2-yl, each of which is optionally substituted by $C_1$–$C_4$-alkyl.

The term aryl is understood as meaning unsubstituted or substituted aryl having preferably 6 to 10 C atoms in the aryl moiety. Phenyl and naphthyl are preferred. The aryl groups can contain 1 to 3 identical or different substituents from the series comprising halogen (in particular chlorine, bromine and/or fluorine), $C_1$–$C_4$-alkyl, $C_1$–$C_4$-alkoxy or $C_1$–$C_4$-alkylthio, halogeno-$C_1$–$C_2$-alkyl (such as trifluoromethyl, difluoromethyl), cyano, nitro, alkylamino, alkanoylamino, arylcarbonylamino, amino or hydroxyl.

Aralkyl is understood as meaning combinations of the above-defined aryl groups having lower alkyl radicals, preferably the benzyl and phenethyl radical.

The term hetaryl is understood as meaning five- or six-membered, optionally substituted aromatic rings containing oxygen and/or 1 to 2 nitrogen atoms, such as, for example the pyridyl or furyl radicals.

Formula (I) provides a general definition of the cyanoalkene derivatives according to the invention.

Preferred compounds of the formula (I) are those in which
R represents optionally substituted $C_1$–$C_{12}$-alkyl, $C_5$–$C_7$-cycloalkyl, aryl or aralkyl and
$R^1$ represents CN, NCS, NH-$C_1$–$C_{12}$-alkyl, imidazolyl, in each case optionally substituted morpholin or thiophenyl or SCN.

Particularly preferred compounds of the formula (I) are those in which
R represents in each case optionally substituted $C_1$–$C_6$-alkyl, cyclohexyl or aryl and
$R^1$ represents SCN.

Very especially preferred compounds of the formula (I) are those in which
represents $C_1$–$C_6$-alkyl or optionally substituted phenyl and
$R^1$ represents SCN.

The compounds of the formula (I) according to the invention are obtained by reacting cyanoalkene halides of the formula (II),

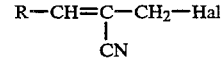

in which R has the abovementioned meaning and hal represents chlorine or bromine, with a reactant of the formula (III) Y—$R^1$ in which $R^1$ has the abovementioned meaning and Y represents hydrogen, sodium, potassium or trimethylsilyl, in an inert solvent.

Y=H, Na, K, TMS.

The reagent of the general formula (II), which is required as starting compound, is obtained from a compound of the general formula (IV) by a route known from the literature (cf., for example, J. Org. Chem. 41 (1976), 20, 3241; J. Org. Chem. 42 (1977), 12, 2094; J. Org. Chem. 28 (1963), 8, 1983; Synth. Commun. 15 (1985), 12, 1067) according to the following equation.

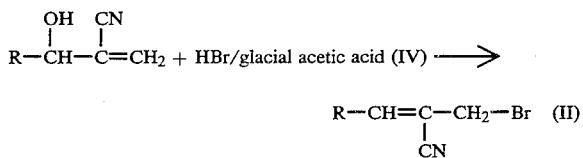

Alternatively, it is also possible to use the corresponding chlorine compound which, in turn, can be obtained by reacting the compound (IV) with thionyl chloride:

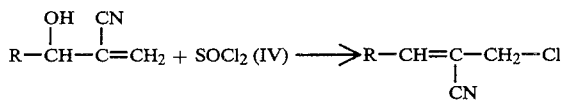

The acrylonitrile derivatives of the general formula (IV) are known compounds and can be obtained as described, for example, in DE-OS (German Published Specification) 2,155,133.

Solvents which are suitable for the reaction and which may be mentioned are, for example, alcohols such as methanol, ethanol, propanol, ethers such as diethyl ether, dioxane, tetrahydrofuran, ketones such as acetone or methyl ethyl ketone; and DMF, DMSO, acetonitrile, if appropriate as a mixture with water.

The reaction is carried out at temperatures from 0° C. to 60° C., preferably at temperatures from 20° to 40° C.

When carrying out the process according to the invention, 1 to 1.2 mol of the reactant of the formula (III) is employed per mole of the cyanoalkene halide compound of the formula (II).

To accelerate the reaction, it can be advantageous in some cases to add an acid acceptor to the reaction mixture. Bases such as, for example, pyridine, collidine or triethylamine are suitable for this purpose.

Work-up and isolation of the cyanoalkene compounds of the formula (I) are carried out by customary methods and are illustrated in greater detail in the examples.

The compounds of the general formula (I) according to the invention are understood as meaning the isomer mixtures (Z/E form) as well as the respective pure E or Z isomers.

The active compounds or compositions according to the invention have a powerful action against microorganisms. They are used in the protection of materials for protecting industrial materials: they are active especially against moulds, wood-discolouring and wood-destroying fungi and bacteria as well as against yeasts, algae, organisms with grow on under water paints and slime organisms. The following genera of microorganisms may be mentioned by way of example, but without limitation:

Alternaria such as *Alternaria tenuis*, Aspergillus such as *Aspergillus niger* and *Aspergillus terreus*, Aureobasidium such as *Aureobasidium pullulans*, Chaetomium such as *Chaetomium globosum*, Cladosporium such as *Cladosporium herbarum*, Coniophora such as *Coniophora puteana*, Gliocladium such as *Gliocladium virens*, Lentinus such as *Lentinus tigrinus*, Paecilomyces such as *Paecilomyces varioti*, Penicillium such as *Penicillium brevicaule*, *Penicillium glaucum* and *Penicillium pinophilum*, Polyporus such as *Polyporus versicolor*, Sclerophoma such as *Sclerophoma pityophila*, Streptoverticillium such as *Streptoverticillium reticulum*, Trichoderma such as *Trichoderma viride*, Trichophyton such as *Trichophyton mentagrophytes*; Escherichia such as *Escherichia coli*, Pseudomonas such as *Pseudomonas areuginosa*, Staphylococcus such as *Staphylococcus aureus*; Candida such as *Candida albicans*. Enteromorpha such as *Enteromorpha intestinalis*.

The amount of active compounds employed depends on the nature and the occurrence of the microorganisms, the microbial count and the medium. The optimum dosage rate can be determined by test series every time the active compound is used. However, in general, an application rate of 0.001 to 20 % by weight, preferably 0.05 to 10 % by weight, of the active compound mixtures, based on the material to be protected, is sufficient.

The new active compounds can be used as such, in the form of concentrates or generally customary formulations such as powders, granules, solutions, suspensions, emulsions or pastes.

The formulations mentioned can be prepared in a manner known per se, for example by mixing the active compounds with solvents or diluents, emulsifiers, dispersers and/or binders or fixatives, if appropriate desiccants and UV stabilisers and, if appropriate, colorants and pigments, and other processing auxiliaries.

Suitable solvents or diluents are organochemical solvents or solvent mixtures and/or a polar organic solvent or solvent mixtures and/or an oily, or oil-type, organochemical solvent or solvent mixture and/or water, preferably with an emulsifier and/or wetting agent. Customary water-insoluble oily or oil-type solvents of low volatility which are preferably used are the particular mineral oils/mineral-oil-containing solvent mixtures or their aromatic fractions. Examples which may be mentioned are, besides spindle oils and monochloronaphthaline, white spirit, petroleum or alkylbenzenes. The boiling ranges of these solvents (solvent mixtures) of low volatility cover the range of approx. 170° C. to a maximum of 350° C.

The above-described oily or oil-type solvents of low volatility can in some cases be replaced by organochemical solvents of greater volatility.

To prepare a wood preservative, it is preferred to replace some of the above-described solvent or solvent mixture by a polar organochemical solvent or solvent mixture. Solvents which are preferably used in this context are those which contain hydroxyl groups, ester groups, ether groups or mixtures of this functionality. Esters or glycol ether may be mentioned by way of example. Binders according to the invention are understood as meaning synthetic resins, binding drying oils, for example based on acrylic resins, vinyl resins, polyester resins, polyurethane resins, alkyd resins, phenol resins, hydrocarbon resins and silicon resins, which can be diluted with water or can be dissolved, dispersed or emulsified in organochemical solvents. The binder used can be employed in the form of a solution, emulsion or dispersion. Mixtures of alkyd resins and drying vegetable oil are preferably used. Alkyd resins containing between 45 and 70% of oil are particularly preferred.

All or some of the binder mentioned can be replaced by a fixative mixture or a plasticiser mixture. These additives are intended to prevent evaporation of the active compounds as well as crystallisation or precipitation. They preferably replace 0.01 to 30% of the binder (based on 100% of the binder employed).

The plasticisers are from the chemical classes or phthalic esters such as dibutyl phthalate, diocytyl phthalate or benzyl butyl phthalate, phosphates such as tributyl phosphate, adipates such as di-(2-ethylhexyl) adipate, stearates such as butyl stearate and amyl stearate, oleates such as butyl oleate, glycerol ethers or higher-molecular-weight glycol ethers, glycerol esters as well as p-toluene sulphonates.

Fixatives are chemically based on polyvinyl alkyl ethers such as, for example, polyvinyl methyl ether, or ketones such as benzophenone and ethylbenzophenone.

A preferred solvent of the compound is water, if appropriate in the form of a mixture with one or more of the abovementioned solvents or diluents, emulsifiers and dispersants.

Industrial materials are, according to the invention, non-live materials which have been prepared for use in industry. For example, industrial materials which are intended to be protected by active compounds according to the invention from microbial change or destruction can be glues, sizes, paper and board, textiles, leather, wood, paints and plastic articles, cooling lubricants and other materials which can be infested with, or destroyed by, microorganisms. Parts of production plants, for example cooling-water circuits, which can be impaired by the multiplication of microorganisms may also be mentioned within the scope of the materials to be protected. Industrial materials which are preferred within the scope of the invention are glues, sizes, papers and boards, leather, wood, paints, cooling lubricants, aqueous hydraulic fluids and cooling circuits and, in general, aqueous functional fluids.

The activity and the spectrum of action of the active compounds according to the invention, or of the agents, concentrates or, quite generally, formulations to be prepared therewith, can be increased when, if appropriate, other antimicrobially active compounds, fungicides, bactericides, herbicides, insecticides or other active compounds for increasing the spectrum of action or for achieving specific effects, such as, for example, the additional protection against insects, are added. These mixtures can have a broader spectrum of action than the compounds according to the invention.

In many cases, this results in synergistic effects, i.e. the activity of the mixture is greater than the activity of the individual components. Particularly favourable components are, for example, the following compounds:

sulphenamides such as dichlofluanid (Euparen), tolylfluanid (methyleuparen), folpet, fluorfolpet;

benzimidazoles, such as carbendazim (MBC), benomyl, fuberidazole, thiabendazole or their salts;

thiocyanates such as thiocyanatomethylthiobenzothiazole (TCMTB), methylene bisthiocyanate (MBT);

quarternary ammonium compounds such as benzyldimethyl-tetradecylammonium chloride, benzyldimethyl-dodecyl-ammonium chloride, didecyldimethyl-ammonium chloride;

morpholine derivatives such as $C_{11}$-$C_{14}$-4-alkyl-2,6-dimethyl-morpholine homologues (tridemorph), ($\pm$)-cis-4-[3-tert-butylphenyl)-2-methylpropyl]-2,6-dimethylmorpholine (fenpropimorph), falimorph;

phenols such as o-phenylphenol, tribromophenol, tetrachlorophenol, pentachlorophenol, 3-methyl-4-chlorophenol, dichlorophene, chlorophene or their salts;

azoles such as triadimefon, triadimenol, bitertanol, tebuconazole, propiconazole, azaconazole, hexaconazole, prochloraz;

iodopropargyl derivatives such as iodopropargylbutylcarbamate (IPBC), iodopropargyl chlorophenylformal, iodopropargyl-phenylcarbamate, iodopropargyl-hexylcarbamate, iodopropargyl-cyclohexylcarbamate, iodopropargyl oxyethylphenylcarbamate;

iodine derivatives such as diiodomethyl p-aryl sulphones, for example diiodomethyl p-tolyl sulphone;

bromine derivatives such as bronopol or bronidox;

isothiazolinones such as N-methylisothiazolin-3-one, 5-chloro-N-methylisothiazolin-3-one, 4,5-dichloro-N-octylisothiazolin-3-one, N-octylisothiazolin-3-one (octhilinone);

benzisothiazolinones, cyclopentene isothiazolines;

pyridines such as 1-hydroxy-2-pyridinthione (and their Na, Fe, Mn, Zn, salts), tetrachloro-4-methylsulphonylpyridine;

metal soaps such as tin naphthenate, tin oc-toate, tin 2-ethylhexanoate, tin oleate, tin phosphate, tin benzoate, copper naphthenate, copper oc-toate, copper 2-ethylhexanoate, copper oleate, copper phosphate, copper benzoate, zinc naphthenate, zinc oc-toate, zinc 2-ethylhexanoate, zinc oleate, zinc phosphate and zinc benzoate, and oxides such as TBTO, $Cu_2O$, CuO, ZnO;

organic tin compounds such as tributyltin naphthenate and tributyltin oxide;

dialkyldithiocarbamates such as Na salts and Zn salts of dialkyldithiocarbamates, tetramethyldiuramidisulphide (TMTD);

nitriles such as 2,4,5,6-tetrachloroisophthalonitrile (chlorthalonil) and other microbicides having activated halogen groups such as Cl-Ac, MCA, tectamer;

benzothiazoles such as 2-mercaptobenzothiazole;

quinolines such as 8-hydroxyquinoline;

formaldehyde-releasing compounds such as benzyl alcohol mono(poly)hemiformal, oxazolidines, hexahydro-s-triazines, N-methylolchloroacetamide;

tris-N-(cyclohexyldiazeniumdioxy)-aluminium, N-(cyclohexyldiazeniumdioxy)-tributyltin, or potassium salts bis-N-(cyclohexyldiazeniumdioxy)-copper.

The following are preferably employed as insecticides:

Phosphates such as azinphos-ethyl, azinphos-methyl, (1-(4-chlorophenyl)-4-(O-ethyl, S-propyl)phosphoryloxypyrazole (TIA-230), chloropyrifos, coumaphos, demeton, demeton-S-methyl, diazinon, dichlorvos, dimethoate, ethoprophos, etrimfos, fenitrothion, fention, heptenophos, parathion, parathion-methyl, phosalone, phoxion, pirimiphos-ethyl, pirimiphos-methyl, profenofos, prothiofos, sulprofos, triazophos and trichlorophon.

Carbamates, such as aldicarb, bendiocarb, BPMC (2-(1-methylpropyl)phenylmethyl carbamate), butocarboxim, butoxycarboxim, carbaryl, carborfuran, carbosulfan, cloethocarb, isoprocarb, methomyl, oxamyl, pirimicarb, promecarb, propoxur and thiodicarb.

Pyrethroids such as allethrin, alphamethrin, bioresmethrin, byfenthrin (FMC 54 800), cycloprothrin, cyfluthrin, decamethrion, cyhalothrin, cypermethrin, deltamethrin, alpha-cyano-3-phenyl-2-methylbenzyl 2,2-dimethyl-3-(2-chloro-2-trifluoromethylvinyl)cyclopropanecarboxylate, fenpropathrin, fenfluthrin, fenvalerate, flucythrinate, flumethrin, fluvalinate, permethrin and resmethrin; nitroimides such as 1-[(6-chloro-3-pyridinyl)-methyl]-4,5-dihydro-N-nitro-1H-imidazol-2-amine(imidacloprid).

Organosilicon compounds, preferably dimethyl(phenyl)-silylmethyl 3-phenoxybenzyl ethers, for example dimethyl(4-ethoxyphenyl)-silylmethyl 3-phenoxybenzyl ether or dimethyl(phenyl)-silylmethyl 2-phenoxy-6-pyridylmethyl ethers, such as, for example, dimethyl(9-ethoxyphenyl)-silylmethyl 2-phenoxy-6-pyridylmethyl ether, or (phenyl)[3-(3-phenoxyphenyl)-propyl](dimethyl)-silanes such as, for example, (4-ethoxyphenyl)-[3-(4-fluoro-3-phenoxyphenyl)-propyl]-dimethyl-silane.

Other suitable active compounds are algicides, molluscicides, active compounds against sea animals which populate, for example, ships' bottom paints.

The microbicidal compositions or concentrates used for the protection of industrial materials contain the active compounds according to the invention in a concentration from 0.01 to 95% by weight, in particular 0.01 to 60% by weight, in addition too, if appropriate, 0.001 to 10% by weight of a suitable further fungicide, insecticide, or a further active compound as mentioned above.

The active compounds or compositions according to the invention allow the previously available microbicidal compositions to be replaced in an advantageous manner by more effective compositions. They show good stability and have, in an advantageous manner, a broad spectrum of action.

The examples which follow are intended to illustrate the invention without limiting it thereto. Parts and percentages are parts by weight and percentages by weight, respectively.

EXAMPLE 1

26.1 g (0.15 mol) of 1-Ethyl-2-cyano-3-bromo-propene, dissolved in 100 ml of acetonitrile, are first introduced, and 14.6 g (0.15 mol) of potassium rhodanide are added. After a reaction time of 5 hours at 20° C., the reaction has ended. The contents of the flask are then stirred into 500 ml of water, and the product is isolated by extraction with methylene chloride. After drying of the product over Na$_2$SO$_4$ and concentration on a rotary evaporator, 20.5 g of an orange-coloured oil of 1-ethyl-2-cyano-3-thiocyanato-propene remain. The compound is characterised by its $^1$H NMR spectrum (δ(H-olefin)=6.49 ppm).

EXAMPLE 2

15 g (0.065 mol) of 1-n-Hexyl-2-cyano-3-bromo-propene together with 6.6 g (0.065 mol) of n-hexylamine are introduced into 100 ml of tetrahydrofuran at room temperature. 6.6 g (0.065 mol) of triethylamine are added, with stirring, and the mixture obtained is then stirred for 10 hours at room temperature; the mixture is then stirred into 400 ml of water and extracted using methylene chloride, and the solvent is removed in vacuo. 13.2 g of a pale yellow-coloured oil of 1-n-hexyl-2-cyano-3-n-hexylamino-propene remain. The compound is characterised by its $^1$H NMR spectrum (δ(H-olefin)=6.30 ppm).

The following compounds of the formula (I)

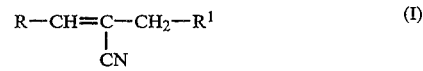

are prepared in an analogous manner and following the general information in the description:

TABLE 1

| Example | R | R$^1$ | Physical data |
|---|---|---|---|
| 3 | n-C$_3$H$_7$ | SCN | δ(CH=): 6.54 ppm (t) |
| 4 | n-C$_4$H$_9$ | SCN | δ(CH=): 6.54 ppm (t) |
| 5 | i-C$_4$H$_9$ | SCN | δ(CH=): 6.55 ppm (t) |
| 6 | s-C$_4$H$_9$ | SCN | δ(CH=): 6.30 ppm (d) |
| 7 | n-C$_6$H$_{13}$ | SCN | δ(CH=): 6.54 ppm (t) |
| 8 | n-C$_{10}$H$_{21}$ | SCN | δ(CH=): 6.54 ppm (t) |
| 9 | C$_6$H$_5$-CH$_2$-CH$_2$- | SCN | δ(CH=): 6.50 ppm (t) |
| 10 | C$_6$H$_5$- | SCN | δ(CH=): 7.21 ppm (s) |
| 11 | 4-Cl-C$_6$H$_4$- | SCN | δ(CH=): 7.16 ppm (s) |
| 12 | 2-Cl-C$_6$H$_4$- | SCN | δ(CH=): 7.59 ppm (s) |
| 13 | 2,6-Cl$_2$-C$_6$H$_3$- | SCN | δ(CH=): 7.40 ppm (s) |
| 14 | 4-CH$_3$-C$_6$H$_4$- | SCN | δ(CH=): 7.16 ppm (s) |
| 15 | 3-CH$_3$-C$_6$H$_4$- | SCN | δ(CH=): 7.44 ppm (s) |
| 16 | 3,4-methylenedioxy-C$_6$H$_3$- | SCN | δ(CH=): 7.08 ppm (s) |
| 17 | naphthyl | SCN | IR: CN 2225 cm$^{-1}$ CN 2160 cm$^{-1}$ |

TABLE 2

| Example | R | R$^1$ | Physical data |
|---|---|---|---|
| 18 | n-C$_3$H$_7$ | NH-n-C$_6$H$_{13}$ | δ(CH=): 6.30 ppm (t) |
| 19 | n-C$_4$H$_9$ | morpholino (N-O ring) | δ(CH=): 6.33 ppm (t) |
| 20 | n-C$_6$H$_{13}$ | morpholino | δ(CH=): 6.33 ppm (t) |
| 21 | n-C$_8$H$_{17}$ | morpholino | δ(CH=): 6.33 ppm (t) |
| 22 | n-C$_{10}$H$_{21}$ | morpholino | δ(CH=): 6.33 ppm (t) |
| 23 | n-C$_4$H$_9$ | piperidino | δ(CH=): 6.29 ppm (t) |
| 24 | n-C$_6$H$_{13}$ | 2,6-dimethylmorpholino | δ(CH=): 6.30 ppm (t) |
| 25 | n-C$_8$H$_{17}$ | 2,6-dimethylmorpholino | δ(CH=): 6.29 ppm (t) |
| 26 | n-C$_{10}$H$_{21}$ | 2,6-dimethylmorpholino | δ(CH=): 6.30 ppm (t) |
| 27 | phenyl | imidazol-1-yl | δ(CH=): 7.08 ppm (s) |
| 28 | naphthyl | imidazol-1-yl | m.p. = 167–69° C. |
| 29 | C$_3$H$_7$ | S-(4-chlorophenyl) | δ(CH=): 6.00 ppm (t) |
| 30 | n-C$_6$H$_{13}$ | S-(4-chlorophenyl) | δ(CH=): 5.99 ppm (t) |

(s) = singlet;
(t) = triplet

Use Example

A. To determine the effectiveness against fungi, the minimum inhibitory concentrations (MICs) of agents according to the invention are determined An agar which has been prepared with brewers' wort and peptone is treated with active compound according to the invention at concentrations of 0.1 mg/l to 5,000 mg/l. After the agar has solidified, it is contaminated with pure cultures of the test organisms listed in Table 1. The MIC is determined after storage for 2 weeks at 28° C. and 60 to 70% relative atmospheric humidity. MIC is the lowest concentration of active compound at which no growth whatsoever of the microspecies used takes place, it can be found in Table I below.

TABLE I

MICs [mg/l] when microorganisms are exposed to cyanoalkene derivatives according to the invention

| Test Organisms | 1 | 3 | 4 | 5 | 6 | 7 | 9 | 10 | 15 |
|---|---|---|---|---|---|---|---|---|---|
| Penicillium brevicaule | 50 | 100 | 20 | 50 | 50 | 20 | 20 | 75 | 50 |
| Chaetomium globosum | 100 | 400 | 50 | 50 | 100 | 15 | 20 | 75 | 75 |
| Aspergillus niger | 100 | 400 | 200 | 400 | 800 | 75 | 400 | 100 | 50 |
| Lentinus tigrinus | 15 | 100 | 20 | 50 | 50 | 20 | 10 | 20 | 75 |
| Sclerophoma pityophila | 5 | 20 | 5 | 10 | 15 | 50 | 5 | 1 | 3 |
| Trichoderma viride | 250 | 300 | 150 | 200 | 400 | 400 | 200 | 100 | 400 |
| Cladosporium herbarum | 75 | 600 | 100 | 200 | 400 | 200 | 200 | 100 | 300 |
| Alternaria tenius | 35 | 200 | 20 | 75 | 200 | 200 | 100 | 50 | 100 |
| Aureobasidium pullulans | 35 | 200 | 35 | 100 | 200 | 50 | 50 | 20 | 150 |
| Staphylococcus | 400 | >800 | 100 | 100 | 100 | <50 | 100 | 50 | >80 |

TABLE I-continued

| | MICs [mg/l] when microorganisms are exposed to cyanoalkene derivatives according to the invention | | | | | | | | |
|---|---|---|---|---|---|---|---|---|---|
| | Examples | | | | | | | | |
| Test Organisms | 1 | 3 | 4 | 5 | 6 | 7 | 9 | 10 | 15 |
| *aureus* | | | | | | | | | |

We claim:

1. A cyanoalkene derivative of the formula

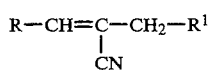

in which
R is an optionally substituted member selected from the group consisting of $C_1$–$C_{12}$-alkyl, alkoxyalkyl, alkylmercaptoalkyl, cycloalkyl, $C_2$–$C_8$-alkenyl, cycloalkenyl, aryl, aralkyl and arylalkenyl, and $R^1$ is SCN.

2. A compound according to claim 1, in which
R is an optionally substituted member selected from the group consisting of $C_1$–$C_{12}$-alkyl, $C_5$–$C_7$-cycloalkyl, aryl and aralkyl, and $R^1$ is SCN.

3. A compound according to claim 1, in which
R is an optionally substituted member selected from the group consisting of $C_1$–$C_6$-alkyl, cyclohexyl and aryl, and
$R^1$ is SCN.

4. A compound according to claim 1, wherein such compound is 1-ethyl-2-cyano-3-thiocyanato-propene.

5. A microbicidal composition comprising a microbicidally effective amount of a compound according to claim 1 and a diluent.

6. A method of combating microorganisms which comprises applying to such microorganisms or to a locus from which it is desired to exclude such microorganisms a microbicidally effective amount of a compound according to claim 1.

7. The method according to claim 6, wherein such compound is 1-ethyl-2-cyano-3-thiocyanato-propene.

* * * * *